US008680109B2

(12) United States Patent
Green

(10) Patent No.: US 8,680,109 B2
(45) Date of Patent: Mar. 25, 2014

(54) COMBINATION PRODUCT COMPRISING SRC KINASE INHIBITOR AZD0530 AND AN ANTIOESTROGEN OR EGFR-TK-INHIBITOR

(75) Inventor: Tim Paul Green, Macclesfield (GB)

(73) Assignee: AstraZeneca AB, Södertälje (SE)

( * ) Notice: Subject to any disclaimer, the term of this patent is extended or adjusted under 35 U.S.C. 154(b) by 50 days.

(21) Appl. No.: 12/714,997

(22) Filed: Mar. 1, 2010

(65) Prior Publication Data

US 2011/0028488 A1 Feb. 3, 2011

Related U.S. Application Data

(63) Continuation of application No. 11/597,940, filed on Nov. 29, 2006, now abandoned, which is a continuation of application No. PCT/GB2005/002102, filed on May 26, 2005.

(30) Foreign Application Priority Data

May 29, 2004 (GB) .................................. 0412074.7

(51) Int. Cl.
*A61K 31/517* (2006.01)
(52) U.S. Cl.
USPC .................................................. 514/266.24
(58) Field of Classification Search
USPC .................................................. 514/266.24
See application file for complete search history.

(56) References Cited

U.S. PATENT DOCUMENTS

| 7,049,438 | B2 | 5/2006 | Hennequin et al. |
| 2006/0142297 | A1 | 6/2006 | Barge |
| 2006/0223815 | A1 | 10/2006 | Curwen et al. |
| 2006/0258642 | A1 | 11/2006 | Hennequin et al. |
| 2009/0099196 | A1 | 4/2009 | Ford et al. |

FOREIGN PATENT DOCUMENTS

| WO | WO 01/94341 | 12/2001 |
| WO | WO 2004/043472 | 5/2004 |
| WO | WO 2004/098604 | 11/2004 |
| WO | WO 2006/064217 | 6/2006 |
| WO | WO 2008/078086 | 7/2008 |

OTHER PUBLICATIONS

Kaklamani V, O'Regan RM. New targeted therapies in breast cancer. Semin Oncol. Apr. 2004;31 (2 Suppl 4):20-5.*
Bharwani et al., "Inibiting the EGFR/HER2 pathway with gefitinib and/or trastuzumab restores tamoxifen sensitivity in HER2-overexpressing tumors", Breast Cancer and Treatment, 82(S1):S1-S14 (2003); 26th Annual San Antonio Breast Cancer Symposium; San Antonio, TX, 2003.
Chabner et al., "Chapter 52-antineoplastic agents", Goodman & Gilman's *The Pharmacological Basis of Therapeutics* 10th ed.,
Hardman et al Eds., McGraw-Hill, NY 2001, 1389-1460 (pp. 1389 and 1440 provided).
Chen et al., "The SRC inhibitor AZD0530 cooperates with anastrozole to inhibit human breast cancer growth in vitro and in vivo" Abstract No. 1470, Abstract/ Poster Presentation at 2008 AACR Annual Meeting, San Diego, CA (Apr. 12-16, 2008).
Chen et al, "Combined Src and aromatase inhibition impairs human breast cancer growth in vivo and bypass pathways are activated in AZD0530-resistant tumors", Clin. Cancer Res. 15(10):3396-3405 (2009).
Chu et al., "p27 Phosphorylation by Src Regulates Inhibition of Cyclin E-Cdk2" Cell 128(2):281-294 (2007).
Herynk et al., "Cooperative action of tamoxifen and c-Src inhibition in preventing the growth of estrogen receptor—positive human breast cancer cells" Mol Cancer Ther. 5(12):3023-3031 (2006).
Hiscox et al., "Tamoxifen resistance in breast cancer cells is accompanied by an enhanced motile and invasive phenotype: Inhibition by gefitinib ('Iressa', ZD1839)" Clinical & Experimental Metastasis 21(3):201-212 (2004).
Hiscox et al., Reduction of in vitro metastatic potential of tamoxifen-resistant breast cancer cells following inhibition of Src kinase activity by AZD0530; European J. Of Cancer, Supplement, 2(8):121-122 (2004).
Hiscox et al., "Elevated Src activity promotes cellular invasion and motility in tamoxifen resistant breast cancer cells" Breast Cancer Research and Treatment 97(3):263-274 (2006).
Hiscox et al., "Src as a therapeutic target in anti-hormone/anti-growth factor-resistant breast cancer" Endocrine-Related Cancer 13(1):S53-S59 (2006).
Hiscox et al. "Combination treatment with AZD0530 and tamoxifen prevents acquired anti-estrogen resistance in breast cancer cells" Abstract A231, Abstract/Poster presentation at ASCO-NCI-EORTC Meeting (Oct. 2007).
Hiscox et al., "Effectiveness of the dual specific Src/Abl kinase inhibitor AZD0530 in combination with tamoxifen in preventing acquired anti-estrogen resistance in breast cancer cells" Journal of Clinical Oncology, 2007 ASCO Annual Meeting Proceedings (Post-Meeting Edition) vol. 25, No. 18S (Jun. 20 Supplement), Abstract No. 14054 (2007).
Loose-Mitchell et al., "Chapter 58—Estrogen and Progestins", Goodman & Gilman's *The Pharmacological Basis of Therapeutics* 10th ed., Hardman et al Eds., McGraw-Hill, NY 2001, 1597-1634 (pp. 1597 and 1613-1617 provided).
Pegram et al., Phase IB pharmacokinetic (PK) study of Src kinase inhibitor AZD0530 plus anastrozole in postmenopausal hormone receptor positive (HR+) metastatic breast cancer (MBC), J. Clin. Oncol. 2010 ASCO Annual Meeting Proceedings (Post-Meeting Edition), 28:15 Suppl. e13074 (2010).
Ple et al., "Discovery of a new class of anilinoquinazoline inhibitors with high affinity and specificity for the tyrosine kinase domain of c-Src" Journal of Medicinal Chemistry 47(4): 871-887 (2004).

(Continued)

*Primary Examiner* — Paul Zarek
(74) *Attorney, Agent, or Firm* — Morgan, Lewis & Bockius LLP

(57) ABSTRACT

The invention relates to a combination for use in the synergistic treatment of breast cancer comprising an antioestrogen and the Src kinase inhibitor AZD0530, a combination for the synergistic treatment of cancer comprising an EGFR TKI and the Src kinase inhibitor AZD0530 and a triple combination for the synergistic treatment of breast cancer comprising an antioestrogen, an EGFR TKI and the Src kinase inhibitor AZD0530.

5 Claims, No Drawings

(56) References Cited

OTHER PUBLICATIONS

Stedman's Medical Dictionary, 27th ed., Lippincott, Eilliams & Wilkins, Baltimore, 2000.

Wheeler et al, "Novel approaches in oncology at AstraZeneca", European Journal of Cancer, Supplement, 1(8):3-8 (2003).

Gee et al., Proceedings of the 1st Tenovus/AstraZeneca Workshop on "Therapeutic resistance in breast cancer: Impact of growth factor signalling pathways and implications for future treatment", Consensus Statement, Endocrine Related Cancer, 12:S1-S7 (2005).

Gee et al., "Understanding endocrine resistance: the critical need for sequential samples from clinical breast cancer and novel in vitro models", Breast Cancer Research, 7(5):187-189 (Oct. 2005).

Giantonio, "Goldie-Coldman and bevacizumab beyond disease progression", Nature Reviews/Clinical Oncology, 6:311-312 (Jun. 2009).

Keating et al., "Therapy's shadow: a short history of the study of resistance to cancer chemotherapy", Frontiers in Pharmacology, vol. 4, Article 58, pp. 1-11 (May 2013).

Knowlden et al., "Insulin-Like Growth Factor-I Receptor Signaling in Tamoxifen-Resistant Breast Cancer: A Supporting Role to the Epidermal Growth Factor Receptor", Endocrinology, 146(11):4609-4618 (Nov. 2005).

Migliaccio et al., "Activation of the Src/p21ras/Erk pathway by progesterone receptor via cross-talk with estrogen receptor", The EMBO Journal, 17(7):2008-2018 (1998).

Migliaccio et al., "Steroid Receptor Regulation of Epidermal Growth Factor Signaling through Src in Breast and Prostate Cancer Cells: Steroid Antagonist Action", Cancer Research, 65:10585-10593 (Nov. 2005).

\* cited by examiner

US 8,680,109 B2

COMBINATION PRODUCT COMPRISING SRC KINASE INHIBITOR AZDO530 AND AN ANTIOESTROGEN OR EGFR-TK-INHIBITOR

This application is a Continuation application of copending U.S. patent application Ser. No. 11/597,940, filed Nov. 29, 2006, which is a U.S. National Phase Application of International Application No. PCT/GB2005/02102, filed May 26, 2005, which claims the benefit of Great Britain Patent Application No. 0412074.7, filed May 29, 2004, all of which are hereby incorporated by reference in their entirety In a first aspect, the present invention relates to a combination comprising an antioestrogen and a particular inhibitor of the Src family of non-receptor tyrosine kinases. The combination of the invention is useful in a method for the treatment of cancer, particularly of breast cancer, or in a method for the delay of the progression of such cancers. The invention also relates to a pharmaceutical composition comprising such a combination and to the use thereof in the manufacture of a medicament for use in the treatment of cancer or in the manufacture of a medicament for use in the delay of the progression of cancer.

In a further aspect, the invention relates to a combination comprising an epidermal growth factor receptor (EGFR) tyrosine kinase (TK) inhibitor and a particular inhibitor of the Src family of non-receptor tyrosine kinases. This combination of the invention is useful in a method for the treatment of cancer, particularly of breast cancer, colorectal cancer, prostate cancer, non-small cell lung cancer and head and neck cancer, or in a method for the delay of the progression of such cancers. This aspect of the invention also relates to a pharmaceutical composition comprising such a combination and to the use thereof in the manufacture of a medicament for use in the treatment of cancer, particularly of lung cancer, colorectal cancer, breast cancer, prostate cancer and head and neck cancer, or in the manufacture of a medicament for use in the delay of the progression of such cancers.

In a further aspect, the invention relates to a combination comprising an antioestrogen, an EGFR TK inhibitor and a particular inhibitor of the Src family of non-receptor tyrosine kinases. The combination of the invention is useful in a method for the treatment of cancer particularly of breast cancer, or in a method for the delay of the progression of such cancers. This aspect of the invention also relates to a pharmaceutical composition comprising such a combination and to the use thereof in the manufacture of a medicament for use in the treatment of cancer or in the manufacture of a medicament for use in the delay of the progression of cancer.

Current options for treating cancer include surgical resection, external beam radiation therapy and/or systemic chemotherapy. These are partially successful in some forms of cancer but are less successful in others. There is a clear need for new therapeutic treatments for treating cancer.

Many of the current treatment regimes for cell proliferation diseases such as cancer utilise compounds which inhibit DNA synthesis. Such compounds are toxic to cells generally but their toxic effect on rapidly dividing cells such as tumour cells can be beneficial. Alternative approaches to anti-tumour agents which act by mechanisms other than the inhibition of DNA synthesis have the potential to display enhanced selectivity of action.

In recent years it has been discovered that a cell may become cancerous by virtue of the transformation of a portion of its DNA into an oncogene i.e. a gene which, on activation, leads to the formation of malignant tumour cells (Bradshaw, *Mutagenesis*, 1986, 1, 91). Several such oncogenes give rise to the production of peptides which are receptors for growth factors. Activation of the growth factor receptor complex subsequently leads to an increase in cell proliferation. It is known, for example, that several oncogenes encode tyrosine kinase enzymes and that certain growth factor receptors are also tyrosine kinase enzymes (Yarden et al., *Ann. Rev. Biochem.*, 1988, 57, 443; Larsen et al., *Ann. Reports in Med. Chem.*, 1989, Chpt. 13). The first group of tyrosine kinases to be identified arose from such viral oncogenes, for example $pp60^{v\text{-}Src}$ tyrosine kinase (otherwise known as v-Src), and the corresponding tyrosine kinases in normal cells, for example $pp60^{c\text{-}Src}$ tyrosine kinase (otherwise known as c-Src).

Receptor tyrosine kinases are important in the transmission of biochemical signals which initiate cell replication. They are large enzymes which span the cell membrane and possess an extracellular binding domain for growth factors such as epidermal growth factor (EGF) and an intracellular portion which functions as a kinase to phosphorylate tyrosine amino acids in proteins and hence to influence cell proliferation. Various classes of receptor tyrosine kinases are known (Wilks, *Advances in Cancer Research*, 1993, 60, 43-73) based on families of growth factors which bind to different receptor tyrosine kinases. The classification includes Class I receptor tyrosine kinases comprising the EGF family of receptor tyrosine kinases such as the EGF, TGFα, Neu and erbB receptors, Class II receptor tyrosine kinases comprising the insulin family of receptor tyrosine kinases such as the insulin and IGF1 receptors and insulin-related receptor (IRR) and Class DI receptor tyrosine kinases comprising the platelet-derived growth factor (PDGF) family of receptor tyrosine kinases such as the PDGFα, PDGFβ and colony-stimulating factor 1 (CSF1) receptors.

It is also known that certain tyrosine kinases belong to the class of non-receptor tyrosine kinases which are located intracellularly and are involved in the transmission of biochemical signals such as those that influence tumour cell motility, dissemination and invasiveness and subsequently metastatic tumour growth (Ullrich et al., *Cell*, 1990, 61, 203-212, Bolen et al., *FASEB J.*, 1992, 6, 3403-3409, Brickell et al., *Critical Reviews in Oncogenesis*, 1992, 3, 401-406, Bohlen et al., *Oncogene*, 1993, 8, 2025-2031, Courtneidge et al., *Semin. Cancer Biol.*, 1994, 5, 239-246, Lauffenburger et al., *Cell*, 1996, 84, 359-369, Hanks et al., *BioEssays*, 1996, 19, 137-145, Parsons et al., *Current Opinion in Cell Biology*, 1997, 9, 187-192, Brown et al., *Biochimica et Biophysica Acta*, 1996, 1287, 121-149 and Schlaepfer et al., *Progress in Biophysics and Molecular Biology*, 1999, 71, 435-478). Various classes of non-receptor tyrosine kinases are known including the Src family such as the Src, Lyn, Fyn and Yes tyrosine kinases, the Abl family such as Abl and Arg and the Jak family such as Jak 1 and Tyk 2.

It is known that the Src family of non-receptor tyrosine kinases are highly regulated in normal cells and in the absence of extracellular stimuli are maintained in an inactive conformation. However, some Src family members, for example c-Src tyrosine kinase, is frequently significantly activated (when compared to normal cell levels) in common human cancers such as gastrointestinal cancer, for example colon, rectal and stomach cancer (Cartwright et al., *Proc. Natl. Acad. Sci. USA*, 1990, 87, 558-562 and Mao et al., *Oncogene*, 1997, 15, 3083-3090), and breast cancer (Muthuswamy et al., *Oncogene*, 1995, 11, 1801-1810). The Src family of non-receptor tyrosine kinases has also been located in other common human cancers such as non-small cell lung cancers (NSCLCs) including adenocarcinomas and squamous cell cancer of the lung (Mazurenko et al., *European Journal of Cancer*, 1992, 28, 372-7), bladder cancer (Fanning et al., *Cancer Research*, 1992, 52, 1457-62), oesophageal cancer (Jankowski et al., *Gut,* 1992, 33, 1033-8), cancer of the prostate, ovarian cancer (Wiener et al., *Clin. Cancer Research,* 1999, 5, 2164-70) and pancreatic cancer (Lutz et al., *Biochem. and Biophys. Res. Comm.,* 1998, 243, 503-8). As further human tumour tissues are tested for the Src family of non-receptor tyrosine kinases it is expected that its widespread prevalence will be established.

It is further known that the predominant role of c-Src non-receptor tyrosine kinase is to regulate the assembly of focal adhesion complexes through interaction with a number of cytoplasmic proteins including, for example, focal adhesion kinase and paxillin. In addition c-Src is coupled to signalling pathways that regulate the actin cytoskeleton which facilitates cell motility. Likewise, important roles are played by the c-Src, c-Yes and c-Fyn non-receptor tyrosine kinases in integrin mediated signalling and in disrupting cadherin-dependent cell-cell junctions (Owens et al., *Molecular Biology of the Cell,* 2000, 11, 51-64 and Klinghoffer et al., *EMBO Journal,* 1999, 18, 2459-2471). Cellular motility is necessarily required for a localised tumour to progress through the stages of dissemination into the blood stream, invasion of other tissues and initiation of metastatic tumour growth. For example, colon tumour progression from localised to disseminated, invasive metastatic disease has been correlated with c-Src non-receptor tyrosine kinase activity (Brunton et al., *Oncogene,* 1997, 14, 283-293, Fincham et al., *EMBO J,* 1998, 17, 81-92 and Verbeek et al., *Exp. Cell Research,* 1999, 248, 531-537).

Accordingly it has been recognised that an inhibitor of such non-receptor tyrosine kinases should be of value as a selective inhibitor of the motility of tumour cells and as a selective inhibitor of the dissemination and invasiveness of mammalian cancer cells leading to inhibition of metastatic tumour growth. In particular an inhibitor of such non-receptor tyrosine kinases should be of value as an anti-invasive agent for use in the containment and/or treatment of solid tumour disease.

It is stated in International Patent Applications WO 01/94341 and WO 02/16352 that the Src kinase inhibitors disclosed therein may be administered as a sole therapy or may involve, in addition to the quinazoline derivatives of those inventions, conventional surgery or radiotherapy or chemotherapy. Such chemotherapy was stated to include one or more of the following categories of anti-tumour agents:—

(i) other anti-invasion agents (for example metalloproteinase inhibitors like marimastat and inhibitors of urokinase plasminogen activator receptor function);

(ii) antiproliferative/antineoplastic drugs and combinations thereof, as used in medical oncology, such as alkylating agents (for example cis-platin, carboplatin, cyclophosphamide, nitrogen mustard, melphalan, chlorambucil, busulphan and nitrosoureas); antimetabolites (for example antifolates such as fluoropyrimidines like 5-fluorouracil and tegafur, raltitrexed, methotrexate, cytosine arabinoside and hydroxyurea, or, for example, one of the preferred antimetabolites disclosed in European Patent Application No. 562734 such as (2S)-2-{o-fluoro-p-[N-{2,7-dimethyl-4-oxo-3,4-dihydroquinazolin-6-ylmethyl)-N-(prop-2-ynyl) amino]benzamido}-4-(tetrazol-5-yl)butyric acid); antitumour antibiotics (for example anthracyclines like adriamycin, bleomycin, doxorubicin, daunomycin, epirubicin, idarubicin, mitomycin-C, dactinomycin and mithramycin); antimitotic agents (for example vinca alkaloids like vincristine, vinblastine, vindesine and vinorelbine and taxoids like taxol and taxotere); and topoisomerase inhibitors (for example epipodophyllotoxins like etoposide and teniposide, amsacrine, topotecan and camptothecin);

(iii) cytostatic agents such as antioestrogens (for example tamoxifen, toremifene, raloxifene, droloxifene and iodoxyfene), antiandrogens (for example bicalutamide, flutamide, nilutamide and cyproterone acetate), LHRH antagonists or LHRH agonists (for example goserelin, leuprorelin and buserelin), progestogens (for example megestrol acetate), aromatase inhibitors (for example as anastrozole, letrazole, vorazole and exemestane) and inhibitors of 5α-reductase such as finasteride;

(iv) inhibitors of growth factor function, for example such inhibitors include growth factor antibodies, growth factor receptor antibodies, tyrosine kinase inhibitors and serine/threonine kinase inhibitors, for example inhibitors of the epidermal growth factor family (for example the EGFR tyrosine kinase inhibitors N-(3-chloro-4-fluorophenyl)-7-methoxy-6-(3-morpholinopropoxy)quinazolin-4-amine (ZD1839), N-(3-ethynylphenyl)-6,7-bis(2-methoxyethoxy)quinazolin-4-amine (CP 358774) and 6-acrylamido-N-(3-chloro-4-fluorophenyl)-7-(3-morpholinopropoxy)quinazolin-4-amine (CI 1033)), for example inhibitors of the platelet-derived growth factor family and for example inhibitors of the hepatocyte growth factor family; and (v) antiangiogenic agents such as those which inhibit vascular endothelial growth factor such as the compounds disclosed in International Patent Applications WO 97/22596, WO 97/30035, WO 97/32856 and WO 98/13354 and those that work by other mechanisms (for example linomide, inhibitors of integrin αvβ3 function and angiostatin).

Combination of an Antioestrogen and the Src Inhibitor AZD0530

Early and advanced carcinomas of the breast are generally hormone-dependent and, thereby, sensitive to inhibition of oestrogen-driven growth signalling by way of the oestrogen receptor. Oestrogen ablation may be achieved by way of surgical castration. Preferably, the effects of oestrogens may also be countered using antioestrogen therapy, for example using a non-steroidal antioestrogen such as tamoxifen, toremifene, raloxifene, droloxifene and iodoxyfene, particularly using tamoxifen. The effects of oestrogens may also be countered using other antioestrogen therapies, for example using a steroidal oestrogen receptor down-regulator such as fulvestrant.

It has also been recognised that the growth of certain other cancers such as lung cancers may be hormone-dependent. For example, oestrogen receptors have been detected in lung tumour tissue. Such cancers may, thereby, be sensitive to inhibition of oestrogen-driven growth signalling by way of the oestrogen receptor.

However, resistance to endocrine therapy presents a major obstacle in the treatment of breast cancer. Tumours that respond initially to antihormone treatment later develop resistance that results in tumour progression. In recent years, research has begun to understand more about the mechanisms that underlie the development of resistance to endocrine therapies and disease progression in breast and prostate cancer. In vitro cell models have been developed that reflect the acquisition of resistance to antihormone agents, notably tamoxifen resistance in breast cancer. It has been shown that resistance in MCF7 human breast cancer cells to the antioestrogen tamoxifen is mediated in part by the elevated expression and activation of components of the EGFR signalling pathway (Knowlden et al., *Endocrinology,* 2003, 144, 1032-1044). It has also been shown that growth factor receptors such as EGFR stimulate cell migration by a mechanism that is believed to involve induction of the mitogen-activated protein kinase (MAPK) signalling pathway (Price et al., *Cell.*

*Commun. Adhesion*, 2002, 9, 87-102). The most important factor affecting the mortality of cancer patients is the development in their tumours of cancer cells having an invasive phenotype. Such cells show an enhancement of cell motility and invasiveness which is reflective of disease progression in vivo.

It is known from International Patent Application WO 01/94341 that certain 5-position substituted quinazoline derivatives possess Src kinase inhibitory activity and are anti-invasive agents useful in the treatment of various cancers including breast cancer. The compound 4-(6-chloro-2,3-methylenedioxyanilino)-7-[2-(4-methylpiperazin-1-yl)ethoxy]-5-tetrahydropyran-4-yloxyquinazoline is disclosed as Compound No. 73 within Example 14 therein. That compound is a potent Src kinase inhibitor and it is identified herein by way of the code number AZD0530.

In the present invention, it has been shown that Src kinase activity is increased and is a dominant pathway controlling the increased invasive ability of antihormone resistant cells. It has been shown that inhibition of Src kinase results in a reduction of cell invasion, further suggesting a significant role of Src kinase signalling in such resistant cells. Unexpectedly, it has been found that a particular selection from the generic disclosures of combination therapies mentioned in International Patent Applications WO 01/94341 and WO 02/16352 is very effective. In particular, the combination of an antioestrogen and the Src kinase inhibitor AZD0530, or a pharmaceutically-acceptable salt thereof, produces surprisingly effective results. More specifically, the combination of an antioestrogen and the Src kinase inhibitor AZD0530 produces a greater effect than that achievable by the administration of either an antioestrogen or the Src kinase inhibitor AZD0530 alone.

Whilst there is the disclosure in International Patent Applications WO 01/94341 and WO 02/16352 that the Src kinase inhibitors disclosed therein may be used in combination with antioestrogens (for example tamoxifen, toremifene, raloxifene, droloxifene and iodoxyfene), there is no specific disclosure of the combination use of an antioestrogen and the Src kinase inhibitor AZD0530, nor that any such combination produces surprisingly effective results.

According to the present invention there is provided a combination suitable for use in the synergistic treatment of breast cancer comprising an antioestrogen and the Src kinase inhibitor AZD0530, or a pharmaceutically-acceptable salt thereof.

It is to be understood that term "a combination" envisages the simultaneous, sequential or separate administration of the components of the combination. In one aspect of the invention, "a combination" envisages simultaneous administration of the antioestrogen and the Src inhibitor. In a further aspect of the invention, "a combination" envisages sequential administration of those agents. In another aspect of the invention, "a combination" envisages separate administration of those agents. Where the administration of those agents is sequential or separate, the delay in administering the second component should not be such as to lose the benefit of the synergistic effect of the combination therapy. Thus, for the avoidance of doubt, the present invention provides a combination comprising an antioestrogen and the Src kinase inhibitor AZD5030, or a pharmaceutically-acceptable salt thereof, for use simultaneously, sequentially or separately in the synergistic treatment of breast cancer, or for use simultaneously, sequentially or separately in the synergistic delay of the progression of breast cancer.

A suitable antioestrogen is, for example, a non-steroidal antioestrogen such as tamoxifen, toremifene, raloxifene, droloxifene and iodoxyfene, particularly tamoxifen, or a steroidal oestrogen receptor down-regulator such as fulvestrant. A preferred antioestrogen is tamoxifen or fulvestrant. A more preferred antioestrogen is tamoxifen. The antioestrogen tamoxifen (also known by the AstraZeneca trade name 'Nolvadex') is the trans isomer of 1-(p-2-dimethylaminoethoxyphenyl)-1,2-diphenylbut-1-ene which is disclosed in U.S. Pat. No. 4,536,516. An alternative name for tamoxifen is (Z)-2-[p-(1,2-diphenylbut-1-enyl)phenoxy]ethyldimethylamine.

The steroidal antioestrogen fulvestrant (also known by the AstraZeneca trade name 'Faslodex' and the code number ICI 182,780) is the first in a new class of potent pure antioestrogens which is completely free of the partial agonist, oestrogen-like activity that is associated with conventional antioestrogens like tamoxifen. The compound acts as an oestrogen receptor down-regulator. Fulvestrant has already demonstrated efficacy in clinical trials in women whose breast cancer has progressed following tamoxifen therapy. The chemical name for fulvestrant is 7-α-[9-(4,4,5,5,5-pentafluoropentylsulphinyl)nonyl]oestra-1,3,5(10)-triene-3, 17β-diol and the compound is described in European Patent Application No. 0 138 504 within Example 35 and within Claim 4.

In addition, a suitable antioestrogen includes, for example, a non-steroidal aromatase inhibitor such as anastrozole, letrozole, fadrozole, vorozole and aminoglutethimide or a steroidal aromatase inhibitor such as exemestane and 1-methyl-1, 4-androstadiene-3,17-dione. A preferred antioestrogen aromatase inhibitor is anastrozole, letrozole or exemestane. A more preferred antioestrogen aromatase inhibitor is anastrozole or letrozole. For example, anastrozole (also known by the trade name 'Arimidex') has as active ingredient the compound 2,2'-[5-(1H-1,2,4-triazol-1-ylmethyl)-1,3-phenylene] di(2-methyl-propionitrile), which is disclosed in US Re-issue Pat. No. 36,617. An alternative name for anastrozole is 2,2'-dimethyl-2,2'-[5-(1H-1,2,4-triazol-1-ylmethyl)-1,3-phenylene]bis(propiononitrile).

A suitable pharmaceutically-acceptable salt of AZD0530 is, for example, a pharmaceutically-acceptable acid-addition salt, for example an acid-addition salt with an inorganic or organic acid such as hydrochloric, hydrobromic, sulphuric, trifluoroacetic, citric, maleic or fumaric acid, for example a mono- or di-fumaric acid salt.

As stated hereinbefore, the combination of the present invention comprising an antioestrogen and the Src kinase inhibitor AZD0530 may also be useful in the synergistic treatment of lung cancer as oestrogen receptors have been detected in lung tumour tissue.

The cancer treatment of the present invention includes an anti-tumour effect that may be assessed by conventional means such as the response rate, the time to disease progression and/or the survival rate. Anti-tumour effects of the present invention include, but are not limited to, inhibition of tumour growth, tumour growth delay, regression of tumour, shrinkage of tumour, increased time to regrowth of tumour on cessation of treatment and delay of disease progression. For example, it is expected that when the combination of the present invention is administered to a warm-blooded animal such as a human, in need of treatment for cancer involving a solid tumour, the treatment will produce a beneficial effect, as measured by, for example, one or more of the extent of the anti-tumour effect, the response rate, the time to disease progression and the survival rate.

As described hereinbefore, the combination of the present invention is particularly useful in the synergistic treatment or prophylaxis of breast cancer. According to the present invention, a combination treatment is defined as affording a synergistic effect if the effect is therapeutically superior, as measured by, for example, the extent of the response, the response rate, the time to disease progression or the survival period, to that achievable on dosing one or other of the components of the combination treatment at its conventional dose. For example, the effect of the combination treatment is synergistic if the effect is therapeutically superior to the effect achievable with an antioestrogen or the Src kinase inhibitor AZD0530 alone. Further, the effect of the combination treatment is synergistic if a beneficial effect is obtained in a group of patients that does not respond (or responds poorly) to an antioestrogen or the Src kinase inhibitor AZD0530 alone. In addition, the effect of the combination treatment is defined as affording a synergistic effect if one of the components is dosed at its conventional dose and the other component is dosed at a reduced dose and the therapeutic effect, as measured by, for example, the extent of the response, the response rate, the time to disease progression or the survival period, is equivalent to or better than that achievable on dosing conventional amounts of either one of the components of the combination treatment. In particular, synergy is deemed to be present if the conventional dose of the antioestrogen or Src kinase inhibitor AZD0530 may be reduced without detriment to one or more of the extent of the response, the response rate, the time to disease progression and survival data, in particular without detriment to the duration of the response, but with fewer and/or less troublesome side-effects than those that occur when conventional doses of each component are used.

The therapeutic combination of the present invention may be administered in the form of a suitable pharmaceutical composition. According to this aspect of the invention there is provided a pharmaceutical composition suitable for use in the synergistic treatment of breast cancer which comprises a combination as defined hereinbefore in association with a pharmaceutically-acceptable excipient or carrier.

The compositions described herein may be in a form suitable for oral administration, for example as a tablet or capsule, for parenteral injection (including intravenous, subcutaneous, intramuscular, intravascular or infusion) for example as a sterile solution, suspension or emulsion, for topical administration for example as an ointment or cream, for rectal administration for example as a suppository or the route of administration may be by direct injection into the tumour or by regional delivery or by local delivery. In other embodiments of the present invention the Src kinase inhibitor of the combination treatment may be delivered percutaneously, intravenously or subcutaneously, or by endoscope or into the trachea, the lesion, the peritoneum or the tumour. In general the compositions described herein may be prepared in a conventional manner using conventional excipients or carriers that are well known in the art.

Suitable pharmaceutically-acceptable excipients or carriers for a tablet formulation include, for example, inert excipients such as lactose, sodium carbonate, calcium phosphate or calcium carbonate, granulating and disintegrating agents such as corn starch or alginic acid; binding agents such as gelatin or starch; lubricating agents such as magnesium stearate, stearic acid or talc; preservative agents such as ethyl or propyl 4-hydroxybenzoate, and anti-oxidants, such as ascorbic acid. Tablet formulations may be uncoated or coated either to modify their disintegration and the subsequent absorption of the active ingredient within the gastrointestinal tract, or to improve their stability and/or appearance, in either case using conventional coating agents and procedures well known in the art.

Compositions for oral use may be in the form of hard gelatin capsules in which the active ingredient is mixed with an inert solid excipient, for example, calcium carbonate, calcium phosphate or kaolin, or as soft gelatin capsules in which the active ingredient is mixed with water or an oil such as peanut oil, liquid paraffin or olive oil.

The compositions of the present invention are advantageously presented in unit dosage form.

The antioestrogen component may be administered according to known clinical practice. For example, in the treatment of advanced breast cancer, a daily oral dose of tamoxifen between 0.5 and 100 mg may be used, conveniently a daily dose between 5 and 30 mg is used. If an antioestrogenic aromatase inhibitor component is present, it may be administered according to known clinical practice. For example, a daily oral dose of anastrozole between 0.005 and 25 mg may be used, conveniently a dose between 0.5 and 5 mg is used. For example, a daily oral dose of exemestane between 5 and 200 mg may be used, conveniently a dose between 10 and 40 mg is used.

If fulvestrant is present, it will generally be administered so that an effective, non-toxic dose is given. The size of the dose will naturally vary according to the route of administration to the patient. In general, conventional doses of fulvestrant can be employed. More particularly, a daily dose is administered in the range, for example, from about 10 mg to 5 g, preferably from about 10 mg to 1 g, more preferably from about 10 mg to 300 mg of compound (i.e. about 0.2 mg/kg to 100 mg/kg body weight, preferably from about 0.2 mg/kg to 20 mg/kg body weight, more preferably from about 0.2 mg/kg to 6 mg/kg body weight), given if required in divided doses. Conveniently, a dose of fulvestrant is administered sufficient to achieve a disease response in the patient, doses of fulvestrant which may be used include those which can be administered in a short acting formulation of from 1 to 15 mg a day, dependent upon the route of administration, or in a long acting formulation equivalent to 200 to 300 mg of compound monthly. A preferred route of administration is by intramuscular injection. Doses should be administered so as to achieve blood serum levels of fulvestrant of from 5 to 20 ng/ml. A preferred formulation is to dissolve a suitable dose of fulvestrant, for example 250 mg, in a 5 ml sample of castor oil containing 10% w/v ethanol, 10% w/v benzyl alcohol and 15% w/v benzyl benzoate. Such a formulation should be injected intramuscularly and will provide therapeutic levels of fulvestrant for around 28 days.

The Src kinase inhibitor AZD0530 will generally be administered so that a daily dose in the range, for example, 0.1 mg/kg to 75 mg/kg body weight is received, given if required in divided doses. In general, lower doses will be administered when a parenteral route is employed. Thus, for example, for intravenous administration, a dose in the range, for example, 0.1 mg/kg to 30 mg/kg body weight will generally be used. Similarly, for administration by inhalation, a dose in the range, for example, 0.05 mg/kg to 25 mg/kg body weight will be used. Oral administration is however preferred, particularly in tablet form. Generally, for oral administration, a dose in the range, for example, 0.1 mg/kg to 20 mg/kg body weight will be used. Particularly, an oral dose in the range, for example, 0.2 mg/kg to 10 mg/kg body weight will be used; more particularly, an oral dose in the range, for example, 0.5 mg/kg to 5 mg/kg body weight will be used. Typically, unit dosage forms will contain about 0.5 mg to 0.5 g of the Src kinase inhibitor; more particularly, unit dosage forms will contain about 25 mg to 250 mg of the Src kinase inhibitor.

The dosages and schedules described hereinbefore may be varied according to the particular disease state and the overall condition of the patient. For example, it may be necessary or desirable to reduce the above-mentioned doses of the components of the combination treatment in order to reduce toxicity. Dose scheduling can be determined by the practitioner who is treating any particular patient using his professional skill and knowledge.

It will be appreciated that the pharmaceutical composition according to the present invention includes a composition comprising an antioestrogen and the Src kinase inhibitor AZD0530 and a pharmaceutically-acceptable excipient or carrier. Such a composition conveniently provides the therapeutic combination product of the invention for simultaneous administration in the synergistic treatment of breast cancer.

According to this aspect of the invention there is provided a pharmaceutical composition suitable for use in the synergistic treatment of breast cancer which comprises an antioestrogen, the Src kinase inhibitor AZD0530, or a pharmaceutically-acceptable salt thereof, and a pharmaceutically-acceptable excipient or carrier.

A pharmaceutical composition according to the present invention also includes separate compositions comprising a first composition comprising an antioestrogen and a pharmaceutically-acceptable excipient or carrier, and a second composition comprising the Src kinase inhibitor AZD0530, or a pharmaceutically-acceptable salt thereof, and a pharmaceutically-acceptable excipient or carrier. Such a composition conveniently provides the therapeutic combination of the invention for sequential or separate administration in the synergistic treatment of breast cancer but the separate compositions may also be administered simultaneously.

Conveniently such a pharmaceutical composition of the invention comprises a kit comprising a first container with a suitable composition containing the antioestrogen and a second container with a suitable composition containing the Src kinase inhibitor AZD0530. According to this aspect of the present invention there is provided a kit for use in the synergistic treatment of breast cancer comprising:—
  a) an antioestrogen together with a pharmaceutically-acceptable excipient or carrier, in a first unit dosage form (such as a tablet or capsule);
  b) the Src kinase inhibitor AZD0530, or a pharmaceutically-acceptable salt thereof, together with a pharmaceutically-acceptable excipient or carrier, in a second unit dosage form; and
  c) container means for containing said first and second unit dosage forms.

According to a further aspect of the present invention there is provided a combination as defined hereinbefore for use in the synergistic treatment of breast cancer.

According to this aspect of the invention there is also provided a pharmaceutical composition for use in the synergistic treatment of breast cancer which comprises a combination as defined hereinbefore in association with a pharmaceutically-acceptable excipient or carrier.

A particular surprising benefit of the present invention is that the breast cancer that can be treated with the combination of the invention can be not only breast cancer in patients who have not yet been treated with antioestrogen therapy but also breast cancer that has been treated with antioestrogen therapy and which has not responded to such therapy or which, after initially being treatable with such therapy, has become resistant.

According to a further aspect of the present invention there is provided the use of a combination as defined hereinbefore in the manufacture of a medicament for administration to a warm-blooded animal to provide the synergistic treatment of breast cancer.

According to a further aspect of the invention there is provided the use of a combination as defined hereinbefore in the manufacture of a medicament for administration to a warm-blooded animal to provide the treatment of antioestrogen-resistant breast cancer.

According to a further aspect of the present invention there is provided a method for the synergistic treatment of breast cancer which comprises the administration to a warm-blooded animal that is in need of such treatment of effective amounts of the components of the combination as defined hereinbefore.

According to a further aspect of the present invention there is provided a method for the treatment of antioestrogen-resistant breast cancer which comprises the administration to a warm-blooded animal that is in need of such treatment of effective amounts of the components of the combination as defined hereinbefore.

According to this aspect of the present invention there is also provided a method for the synergistic treatment of breast cancer which comprises the administration to a warm-blooded animal that is in need of such treatment of an effective amount of an antioestrogen as defined hereinbefore before, simultaneously with or after the administration of an effective amount of the Src kinase inhibitor AZD0530, or a pharmaceutically-acceptable salt thereof.

According to this aspect of the present invention there is also provided a method for the synergistic treatment of breast cancer which comprises the simultaneous, sequential or separate administration to a warm-blooded animal that is in need of such treatment of effective amounts of the components of the combination as defined hereinbefore.

According to this aspect of the present invention there is also provided a method for the synergistic treatment of breast cancer which comprises the administration to a warm-blooded animal that is in need of such treatment of an effective amount of an antioestrogen as defined hereinbefore and the simultaneous, sequential or separate administration of an effective amount of the Src kinase inhibitor AZD0530, or a pharmaceutically-acceptable salt thereof.

The present invention also relates to a combination comprising an antioestrogen and the Src kinase inhibitor AZD0530, or a pharmaceutically-acceptable salt thereof, for use in the delay of the progression of breast cancer from a hormonally responsive to a hormonally non-responsive state i.e. to inhibit the transformation of breast cancer cells from a hormone-dependent, non-invasive state into a hormone-independent, more invasive state. Consequently the combination has a beneficial effect on the time to disease progression and the survival rate.

According to this aspect of the present invention there is provided a combination comprising an antioestrogen and the Src kinase inhibitor AZD0530, or a pharmaceutically-acceptable salt thereof, for use in the delay of the progression of breast cancer from a hormonally responsive to a hormonally non-responsive state.

In another aspect, the invention relates to the use of the combination to inhibit the transformation of breast cells into cancerous cells i.e. the combination of compounds provides a breast cancer chemopreventative effect.

In normal human breast epithelium in the premenopausal woman, cells have nuclei of standard size and standard chromatin levels. It is known that there is a series of changes in the appearance of normal breast epithelium as malignancy develops. In normal epithelial tissue, oestrogen stimulates normal growth and induces the expression of the progesterone receptor which allows progesterone to mediate breast epthelial cell growth. Constitutive growth of such epithelial cells comprises the non-oestrogen dependent baseline turnover of cells. In premenopausal women, disease of breast epithelial tissue disease first becomes apparent when, in general, the size of the nuclei has begun to be enlarged and the chromatin levels have begun to be increased. These are pre-malignant changes and at this stage the condition is known (paradoxically) as Ductal Carcinoma In Situ (DCIS). As disease progresses and DCIS cells are transformed into malignant cells, the cells have markedly enlarged nuclei or nucleoli and also markedly increased chromatin levels.

We have found that unexpectedly the combination of the present invention has effects not only on the growth of transformed breast cancer cells but also on the constitutive growth of normal cells and of non-malignant, abnormal cells in the breast. The combination of the present invention may therefore be used to reduce, preferably to inhibit, the transformation of breast cells to a malignant state. The combination of an antioestrogen and the Src kinase inhibitor AZD0530 of the present invention can inhibit the transformation of normal breast cells to a DCIS state. Said combination can also inhibit the transformation of DCIS cells to a malignant state.

It is further expected that the combination will have a beneficial effect in preventing the onset of breast cancer in women genetically predisposed to the disease.

According to this aspect of the present invention there is provided a combination comprising an antioestrogen and the Src kinase inhibitor AZD0530, or a pharmaceutically-acceptable salt thereof, for use in reducing, preferably inhibiting, the transformation of normal breast cells to a DCIS state.

According to this aspect of the present invention there is also provided a combination comprising an antioestrogen and the Src kinase inhibitor AZD0530, or a pharmaceutically-acceptable salt thereof, for use in reducing, preferably inhibiting, the transformation of normal breast cells or DCIS cells to a malignant state.

A combination treatment of the present invention as defined hereinbefore may be administered as a sole therapy or may in addition involve surgery or radiotherapy or the administration of a chemotherapeutic agent.

Surgery may comprise the step of partial or complete tumour resection, prior to, during or after the administration of the combination treatment of the present invention.

Chemotherapeutic agents for optional use with the combination treatment of the present invention may include, for example, the following categories of therapeutic agent:—
  (i) antiproliferative/antineoplastic drugs and combinations thereof as used in medical oncology (for example carboplatin and cisplatin);
  (ii) cytostatic agents, for example inhibitors of growth factor function such as growth factor antibodies, growth factor receptor antibodies (for example the anti-erbB2 antibody trastuzumab and the anti-erbB1 antibody cetuximab), Class I receptor tyrosine kinase inhibitors (for example inhibitors of the epidermal growth factor family), Class II receptor tyrosine kinase inhibitors (for example inhibitors of the insulin growth factor family such as IGF1 receptor inhibitors as described, for example, by Chakravarti et al., *Cancer Research*, 2002, 62, 200-207), serine/threonine kinase inhibitors, farnesyl transferase inhibitors and platelet-derived growth factor inhibitors;
  (iii) antiangiogenic agents such as those which inhibit the effects of vascular endothelial growth factor (for example the anti-vascular endothelial cell growth factor antibody bevacizumab and VEGF receptor tyrosine kinase inhibitors such as 4-(4-bromo-2-fluoroanilino)-6-methoxy-7-(1-methylpiperidin-4-ylmethoxy) quinazoline (ZD6474; Example 2 within WO 01/32651), 4-(4-fluoro-2-methylindol-5-yloxy)-6-methoxy-7-(3-pyrrolidin-1-ylpropoxy)quinazoline (AZD2171; within WO 00/47212), vatalanib (PTK787; WO 98/35985) and SU11248 (WO 01/60814));
  (iv) vascular damaging agents such as the compounds disclosed in International Patent Applications WO 99/02166, WO00/40529, WO 00/41669, WO01/92224, WO02/04434 and WO02/08213;
  (v) biological response modifiers (for example interferon); and
  (vi) a bisphosphonate such as tiludronic acid, ibandronic acid, incadronic acid, risedronic acid, zoledronic acid, clodronic acid, neridronic acid, pamidronic acid and alendronic acid.

For example, the administration of a combination of an antioestrogen, the Src kinase inhibitor AZD0530, or a pharmaceutically-acceptable salt thereof, and ionising radiation may produce anti-cancer effects, such as anti-tumour effects, that are greater than those achieved if the radiation is omitted.

According to this aspect of the present invention there is provided a method for the synergistic treatment of breast cancer which comprises the administration to a warm-blooded animal such as man that is in need of such treatment of an effective amount of an antioestrogen before, simultaneously with or after an effective amount of the Src kinase inhibitor AZD0530, or a pharmaceutically-acceptable salt thereof, and before, simultaneously with or after an effective amount of ionising radiation.

The ionising radiation may be given to said warm-blooded animal such as man within the period of a week before to a week after the administration of the combination of the present invention as defined hereinbefore.

Radiotherapy may be administered according to the known practices in clinical radiotherapy. The dosages of ionising radiation will be those known for use in clinical radiotherapy. The radiation therapy used will include for example the use of γ-rays, X-rays, and/or the directed delivery of radiation from radioisotopes. Other forms of DNA damaging factors are also included in the present invention such as microwaves and UV-irradiation. For example X-rays may be dosed in daily doses of 1.8-2.0 Gy, 5 days a week for 5-6 weeks. Normally a total fractionated dose will lie in the range 45-60 Gy. Single larger doses, for example 5-10 Gy may be administered as part of a course of radiotherapy. Single doses may be administered intraoperatively. Hyperfractionated radiotherapy may be used whereby small doses of X-rays are administered regularly over a period of time, for example 0.1 Gy per hour over a number of days. Dosage ranges for radioisotopes vary widely, and depend on the half-life of the isotope, the strength and type of radiation emitted, and on the uptake by cells.

According to a further aspect of the present invention there is provided the use of a combination as defined hereinbefore in the manufacture of a medicament for administration to a warm-blooded animal such as man that is being treated with ionising radiation to provide the synergistic treatment of breast cancer.

Combination of an EGFR TKI and the Src Inhibitor AZD0530

The present invention also relates to a combination comprising an epidermal growth factor receptor tyrosine kinase inhibitor (hereinafter an "EGFR TKI") and a particular inhibitor of the Src family of non-receptor tyrosine kinases. This combination of the invention is useful in a method for the treatment of cancer.

There is extensive evidence of high expression levels of EGFR in a number of human tumours and that increased expression may correlate with disease progression and a poor prognosis for the patient (Nicholson et al., *Breast Cancer Research Treatment*, 1994, 29, 117-125 and *European Journal of Cancer*, 2001, 37, Supplement 4, S9-15). For example, it has been shown that resistance in MCF7 human breast cancer cells to the antioestrogen tamoxifen is mediated in part by the elevated expression and activation of components of the EGFR signalling pathway (Knowlden et al., *Endocrinology*, 2003, 144, 1032-1044). It was also shown therein that both the basal and TGFα stimulated growth of tamoxifen resistant MCF7 breast cancer cells could be inhibited by the EGFR TKI ZD1839.

Cancers that are amenable to treatment with the combination of this aspect of the present invention include oesophageal cancer, myeloma, hepatocellular, pancreatic and cervical cancer, Ewings tumour, neuroblastoma, kaposis sarcoma, ovarian cancer, breast cancer, colorectal cancer, prostate cancer, bladder cancer, melanoma, lung cancer [including non small cell lung cancer (NSCLC) and small cell lung cancer (SCLC)], gastric cancer, head and neck cancer, brain cancer, renal cancer, lymphoma and leukaemia. More particularly, this combination of the present invention is useful in the treatment of breast cancer, colorectal cancer, prostate cancer, NSCLC and head and neck cancer, or in a method for the delay of the progression of such cancers.

According to this aspect of the present invention there is provided a combination suitable for use in the synergistic treatment of cancer (particularly of breast cancer, colorectal cancer, prostate cancer, non-small cell lung cancer and head and neck cancer) comprising an EGFR TKI, or a pharmaceutically-acceptable salt thereof, and the Src kinase inhibitor AZD0530, or a pharmaceutically-acceptable salt thereof.

It is to be understood that term "a combination" envisages the simultaneous, sequential or separate administration of the components of the combination as described hereinbefore.

It is known that Class I kinases such as the EGF family of receptor tyrosine kinases are frequently present in common human epithelial cancers such as cancer of the prostate (Visakorpi et al., *Histochem. J.*, 1992, 24, 481). Accordingly it has been recognised that an inhibitor of receptor tyrosine kinases should be of value as a selective inhibitor of the growth of prostate carcinomas.

It is known from European Patent Application No. 0566226 and International Patent Applications WO 96/33980 and WO 97/30034 that certain quinazoline derivatives which possess an anilino substituent at the 4-position possess EGFR tyrosine kinase inhibitory activity and are inhibitors of the proliferation of cancer tissue including prostate cancer. It has been disclosed by J R Woodburn et al. in *Proc. Amer. Assoc. Cancer Research*, 1997, 38, 633 and *Pharmacol. Ther.*, 1999, 82, 241-250 that the compound N-(3-chloro-4-fluorophenyl)-7-methoxy-6-(3-morpholinopropoxy)quinazolin-4-amine (also known as gefitinib and by the AstraZeneca trade name 'Iressa'). That compound is a potent EGFR TKI and is identified hereinafter by the code number ZD1839.

It is further known from International Patent Application WO 96/30347 that certain structurally-related quinazoline derivatives possessing an anilino substituent at the 4-position also possess EGFR tyrosine kinase inhibitory activity. It has been disclosed in WO 99/55683 that the compound N-(3-ethynylphenyl)-6,7-bis(2-methoxyethoxy)quinazolin-4-amine, or a pharmaceutically-acceptable salt thereof (linked to the code numbers CP 358774 and OSI-774) is an EGFR TKI. That compound is now known as erlotinib and is identified hereinafter by the code number OSI-774.

It is further known from International Patent Application WO 97/38983 that certain other structurally-related quinazoline derivatives possessing an anilino substituent at the 4-position also possess EGFR tyrosine kinase inhibitory activity. It has been disclosed in *J. Med. Chem.*, 1999, 42, 1803-1815 and WO 00/31048 that the compound 6-acrylamido-N-(3-chloro-4-fluorophenyl)-7-(3-morpholinopropoxy)quinazolin-4-amine (linked to the code numbers PD 183805 and CI 1033) is an EGFR TKI. That compound is identified hereinafter by the code number CI 1033).

It is further known from International Patent Application WO 97/02266 that certain other structurally-related heterocyclic derivatives also possess EGFR tyrosine kinase inhibitory activity. For example, the compound 4-[(1R)-1-phenylethylamino]-6-(4-hydroxyphenyl)-7H-pyrrolo[2,3-d]pyrimidine (linked to the code numbers PKI-166, CGP 75166 and CGP 59326) is an EGFR TKI. That compound is identified hereinafter by the code number PM-166.

It is further known from European Patent Application No. 0787722 and International Patent Applications WO 98/50038, WO 99/09016 and WO 99/24037 that certain other structurally-related quinazoline derivatives possessing an anilino substituent at the 4-position also possess EGFR tyrosine kinase inhibitory activity. For example, the compound N-[4-(3-bromoanilino)quinazolin-6-yl]but-2-ynamide (linked to the code numbers CL-387785 and EKB-785) is an EGFR TKI. That compound is identified hereinafter by the code number CL-387785.

It is further known from Nature Medicine, 2000, 6, 1024-1028 and U.S. Pat. No. 6,002,008 that certain other structurally-related quinoline derivatives possessing an anilino substituent at the 4-position also possess EGFR tyrosine kinase inhibitory activity. For example, the compound 4-(3-chloro-4-fluoroanilino)-3-cyano-6-(4-dimethylaminobut-2(E)-enamido)-7-ethoxyquinoline (identified hereinafter by the code number EKB-569) is an EGFR TKI.

In a suitable combination of the invention, the EGFR TKI is selected from, for example, ZD1839, OSI-774, CI 1033, PKI-166, CL-387785 and EKB-569. Preferably the EGFR TKI component of the combination is ZD1839 or OSI-774. More preferably the EGFR TKI component of the combination is ZD1839.

As stated hereinbefore, a suitable pharmaceutically-acceptable salt of AZD0530 is, for example, a pharmaceutically-acceptable acid-addition salt, for example an acid-addition salt with an inorganic or organic acid such as hydrochloric, hydrobromic, sulphuric, trifluoroacetic, citric, maleic or fumaric acid. Similar pharmaceutically-acceptable salts of the EGFR TKI component of this aspect of the present invention may be employed.

As stated hereinbefore, the combination of the present invention comprising an EGER TKI and the Src kinase inhibitor AZD0530 is useful in the synergistic treatment of cancer. The cancer treatment of the present invention includes an anti-tumour effect that may be assessed by conventional means as described hereinbefore.

The combination treatment of the present invention is defined as affording a synergistic effect if the effect is therapeutically superior using analogous criteria to those described hereinbefore.

A preferred combination according to this aspect of the present invention comprises the EGER TKI ZD1839, or a pharmaceutically-acceptable salt thereof, and the Src kinase inhibitor AZD0530, or a pharmaceutically-acceptable salt thereof.

A further preferred combination according to this aspect of the present invention comprises the EGER TKI OSI-774, or a pharmaceutically-acceptable salt thereof, and the Src kinase inhibitor AZD0530, or a pharmaceutically-acceptable salt thereof.

The therapeutic combination of this aspect of the present invention may be administered in the form of a suitable pharmaceutical composition. According to this aspect of the invention there is provided a pharmaceutical composition suitable for use in the synergistic treatment of cancer which comprises a combination of an EGFR TKI, or a pharmaceutically-acceptable salt thereof, and the Src kinase inhibitor AZD0530, or a pharmaceutically-acceptable salt thereof, in association with a pharmaceutically-acceptable excipient or carrier.

The compositions described in this aspect of the invention may be in any suitable form such as the forms described hereinbefore.

A preferred pharmaceutical composition suitable for use in the synergistic treatment of cancer comprises a combination of the EGFR TKI ZD1839, or a pharmaceutically-acceptable salt thereof, and the Src kinase inhibitor AZD0530, or a pharmaceutically-acceptable salt thereof, in association with a pharmaceutically-acceptable excipient or carrier.

A further preferred pharmaceutical composition suitable for use in the synergistic treatment of cancer comprises a combination of the EGER TKI OSI-774, or a pharmaceutically-acceptable salt thereof, and the Src kinase inhibitor AZD0530, or a pharmaceutically-acceptable salt thereof, in association with a pharmaceutically-acceptable excipient or carrier.

For the EGFR TKI component, a tablet or capsule formulation intended for oral administration will generally contain, for example, from about 20 mg to 1 g of active ingredient. When the EGER TKI is ZD1839, a conventional tablet formulation may be used for oral administration containing 50 mg, 100 mg, 250 mg or 500 mg of active ingredient. Conveniently the daily oral dose of ZD1839 is above 40 mg, for example, in the range 50 to 750 mg, preferably in the range 100 to 500 mg, more preferably in the range 200 to 500 mg. When the EGFR TKI is OSI-774, a conventional tablet formulation may be used for oral administration containing 25 mg, 100 mg or 150 mg of active ingredient. Conveniently the daily oral dose of OSI-774 is in the range 50 to 300 mg, preferably in the range 50 to 200 mg, more preferably in the range 100 to 150 mg.

The Src kinase inhibitor AZD0530 will generally be administered using analogous amounts and routes of administration to those described hereinbefore.

The dosages and schedules described hereinbefore may be varied according to the particular disease state and the overall condition of the patient. For example, it may be necessary or desirable to reduce the above-mentioned doses of the components of the combination treatment in order to reduce toxicity. Dose scheduling can be determined by the practitioner who is treating any particular patient using his professional skill and knowledge.

It will be appreciated that the pharmaceutical composition according to the present invention includes a composition comprising an EGFR TKI and the Src kinase inhibitor AZD0530 and a pharmaceutically-acceptable excipient or carrier. Such a composition conveniently provides the therapeutic combination product of the invention for simultaneous administration in the synergistic treatment of cancer.

According to this aspect of the invention there is provided a pharmaceutical composition suitable for use in the synergistic treatment of cancer which comprises an EGFR TKI, or a pharmaceutically-acceptable salt thereof, the Src kinase inhibitor AZD0530, or a pharmaceutically-acceptable salt thereof, and a pharmaceutically-acceptable excipient or carrier.

A pharmaceutical composition according to the present invention also includes separate compositions comprising a first composition comprising an EGFR TKI, or a pharmaceutically-acceptable salt thereof, and a pharmaceutically-acceptable excipient or carrier, and a second composition comprising the Src kinase inhibitor AZD0530, or a pharmaceutically-acceptable salt thereof, and a pharmaceutically-acceptable excipient or carrier. Such a composition conveniently provides the therapeutic combination of the invention for sequential or separate administration in the synergistic treatment of cancer but the separate compositions may also be administered simultaneously.

Conveniently such a pharmaceutical composition of the invention comprises a kit comprising a first container with a suitable composition containing the EGFR TKI and a second container with a suitable composition containing the Src kinase inhibitor AZD0530. According to this aspect of the present invention there is provided a kit for use in the synergistic treatment of cancer comprising:—
  a) an EGFR TKI, or a pharmaceutically-acceptable salt thereof, together with a pharmaceutically-acceptable excipient or carrier, in a first unit dosage form;
  b) the Src kinase inhibitor AZD0530, or a pharmaceutically-acceptable salt thereof, together with a pharmaceutically-acceptable excipient or carrier, in a second unit dosage form; and
  c) container means for containing said first and second unit dosage forms.

According to a further aspect of the present invention there is provided a combination as defined hereinbefore for use in the synergistic treatment of cancer.

According to this aspect of the invention there is also provided a pharmaceutical composition for use in the synergistic treatment of cancer which comprises a combination as defined hereinbefore in association with a pharmaceutically-acceptable excipient or carrier.

A particular surprising benefit of the present invention is that the cancer that can be treated with the combination of the invention can be not only cancer in patients who have not yet been treated with a growth factor inhibitor but also cancer that has been treated with a growth factor inhibitor, for example with an EGFR TKI, and which has not responded to such therapy or which, after initially being treatable with such therapy, has become resistant.

According to a further aspect of the present invention there is provided the use of a combination as defined hereinbefore in the manufacture of a medicament for administration to a warm-blooded animal to provide the synergistic treatment of cancer.

According to a further aspect of the invention there is provided the use of a combination as defined hereinbefore in the manufacture of a medicament for administration to a warm-blooded animal to provide the treatment of EGFR TKI resistant cancer.

According to a further aspect of the present invention there is provided a method for the synergistic treatment of cancer which comprises the administration to a warm-blooded animal that is in need of such treatment of effective amounts of the components of the combination as defined hereinbefore.

According to a further aspect of the present invention there is provided a method for the treatment of EGFR TKI resistant cancer which comprises the administration to a warm-blooded animal that is in need of such treatment of effective amounts of the components of the combination as defined hereinbefore.

According to this aspect of the present invention there is also provided a method for the synergistic treatment of cancer (including EGFR TKI resistant cancer) which comprises the administration to a warm-blooded animal that is in need of such treatment of an effective amount of an EGFR TKI, or a pharmaceutically-acceptable salt thereof, as defined hereinbefore before, simultaneously with or after the administration of an effective amount of the Src kinase inhibitor AZD0530, or a pharmaceutically-acceptable salt thereof.

According to this aspect of the present invention there is also provided a method for the synergistic treatment of cancer (including EGFR TKI resistant cancer) which comprises the simultaneous, sequential or separate administration to a warm-blooded animal that is in need of such treatment of effective amounts of the components of the combination as defined hereinbefore.

According to this aspect of the present invention there is also provided a method for the synergistic treatment of cancer (including EGFR TKI resistant cancer) which comprises the administration to a warm-blooded animal that is in need of such treatment of an effective amount of an EGFR TKI, or a pharmaceutically-acceptable salt thereof, as defined hereinbefore and the simultaneous, sequential or separate administration of an effective amount of the Src kinase inhibitor AZD0530, or a pharmaceutically-acceptable salt thereof.

A combination treatment of the present invention as defined hereinbefore may be administered as a sole therapy or may in addition involve surgery or radiotherapy or the administration of a chemotherapeutic agent as defined hereinbefore.

Combination of an Antioestrogen, an EGFR TKI and the Src Inhibitor AZD0530

The present invention also relates to a triple combination comprising an antioestrogen, an EGFR tyrosine kinase inhibitor and a particular inhibitor of the Src family of non-receptor tyrosine kinases. This combination of the invention is useful in a method for the treatment of cancer, particularly of breast cancer.

As stated hereinbefore, it has been shown that resistance in MCF7 human breast cancer cells to the antioestrogen tamoxifen is mediated in part by the elevated expression and activation of components of the EGFR signalling pathway. It was also stated that both the basal and TGFα stimulated growth of tamoxifen resistant MCF7 breast cancer cells could be inhibited by the EGFR tyrosine kinase inhibitor ZD1839.

According to this aspect of the present invention there is provided a triple combination suitable for use in the synergistic treatment of breast cancer comprising an antioestrogen, an EGFR TKI, or a pharmaceutically-acceptable salt thereof, and the Src kinase inhibitor AZD0530, or a pharmaceutically-acceptable salt thereof.

It is to be understood that term "a combination" envisages the simultaneous, sequential or separate administration of the components of the combination as described hereinbefore.

A suitable antioestrogen has any of the meanings defined hereinbefore.

A suitable EGFR TKI has any of the meanings defined hereinbefore. In a suitable triple combination of the invention, the EGFR TKI is selected from, for example, ZD1839, OSI-774, CI 1033, PKI-166, CL-387785 and EKB-569. Preferably the EGFR TKI component of the triple combination is ZD1839 or OSI-774. More preferably the EGFR TKI component of the triple combination is ZD1839.

As stated hereinbefore, a suitable pharmaceutically-acceptable salt of the EGFR TKI or of AZD0530 is, for example, a pharmaceutically-acceptable acid-addition salt, for example an acid-addition salt with an inorganic or organic acid such as hydrochloric, hydrobromic, sulphuric, trifluoroacetic, citric, maleic or fumaric acid.

As stated hereinbefore, the triple combination of the present invention is useful in the synergistic treatment of breast cancer. The cancer treatment of the present invention includes an anti-tumour effect that may be assessed by conventional means as described hereinbefore.

The triple combination treatment of the present invention is defined as affording a synergistic effect if the effect is therapeutically superior using analogous criteria to those described hereinbefore.

A preferred triple combination according to this aspect of the present invention comprises an antioestrogen, the EGFR TKI ZD1839, or a pharmaceutically-acceptable salt thereof, and the Src kinase inhibitor AZD0530, or a pharmaceutically-acceptable salt thereof.

A further preferred triple combination according to this aspect of the present invention comprises an antioestrogen, the EGFR TKI OSI-774, or a pharmaceutically-acceptable salt thereof, and the Src kinase inhibitor AZD0530, or a pharmaceutically-acceptable salt thereof.

The triple combinations of the present invention may also be useful in the synergistic treatment of lung cancer as oestrogen receptors have been detected in lung tumour tissue.

The triple combination of this aspect of the present invention may be administered in the form of a suitable pharmaceutical composition. According to this aspect of the invention there is provided a pharmaceutical composition suitable for use in the synergistic treatment of breast cancer which comprises a combination of an antioestrogen, an EGFR TKI, or a pharmaceutically-acceptable salt thereof, and the Src kinase inhibitor AZD0530, or a pharmaceutically-acceptable salt thereof, in association with a pharmaceutically-acceptable excipient or carrier.

The compositions described in this aspect of the invention may be in any suitable form such as the forms described hereinbefore.

A preferred pharmaceutical composition suitable for use in the synergistic treatment of breast cancer comprises a combination of an antioestrogen, the EGFR TKI ZD1839, or a pharmaceutically-acceptable salt thereof, and the Src kinase inhibitor AZD0530, or a pharmaceutically-acceptable salt thereof, in association with a pharmaceutically-acceptable excipient or carrier.

A further preferred pharmaceutical composition suitable for use in the synergistic treatment of breast cancer comprises a combination of an antioestrogen, the EGFR TKI OSI-774, or a pharmaceutically-acceptable salt thereof, and the Src kinase inhibitor AZD0530, or a pharmaceutically-acceptable salt thereof, in association with a pharmaceutically-acceptable excipient or carrier.

Each of the antioestrogen component, the EGFR TKI component, and the Src kinase inhibitor AZD0530 will generally be administered using analogous amounts and routes of administration to those described hereinbefore.

The dosages and schedules described hereinbefore may be varied according to the particular disease state and the overall condition of the patient. For example, it may be necessary or desirable to reduce the above-mentioned doses of the components of the combination treatment in order to reduce toxicity. Dose scheduling can be determined by the practitioner who is treating any particular patient using his professional skill and knowledge.

It will be appreciated that the pharmaceutical composition according to the present invention includes a composition comprising an antioestrogen, an EGFR TKI and the Src kinase inhibitor AZD0530 and a pharmaceutically-acceptable excipient or carrier. Such a composition conveniently provides the therapeutic combination product of the invention for simultaneous administration in the synergistic treatment of breast cancer.

According to this aspect of the invention there is provided a pharmaceutical composition suitable for use in the synergistic treatment of breast cancer which comprises an antioestrogen, an EGFR TKI, or a pharmaceutically-acceptable salt thereof, the Src kinase inhibitor AZD0530, or a pharmaceutically-acceptable salt thereof, and a pharmaceutically-acceptable excipient or carrier.

A pharmaceutical composition according to this aspect of the present invention also includes separate compositions comprising a first composition comprising an antioestrogen and a pharmaceutically-acceptable excipient or carrier, a second composition comprising an EGFR TKI, or a pharmaceutically-acceptable salt thereof, and a pharmaceutically-acceptable excipient or carrier, and a third composition comprising the Src kinase inhibitor AZD0530, or a pharmaceutically-acceptable salt thereof, and a pharmaceutically-acceptable excipient or carrier. Such a composition conveniently provides the therapeutic combination of the invention for sequential or separate administration in the synergistic treatment of cancer but the separate compositions may also be administered simultaneously.

Conveniently such a pharmaceutical composition of the invention comprises a kit comprising a first container with a suitable composition containing the antioestrogen, a second container with a suitable composition containing the EGFR TKI and a third container with a suitable composition containing the Src kinase inhibitor AZD0530. According to this aspect of the present invention there is provided a kit for use in the synergistic treatment of breast cancer comprising:—
 a) an antioestrogen together with a pharmaceutically-acceptable excipient or carrier, in a first unit dosage form (such as a tablet or capsule);
 b) an EGFR TKI, or a pharmaceutically-acceptable salt thereof, together with a pharmaceutically-acceptable excipient or carrier, in a second unit dosage form;
 c) the Src kinase inhibitor AZD0530, or a pharmaceutically-acceptable salt thereof, together with a pharmaceutically-acceptable excipient or carrier, in a third unit dosage form; and
 d) container means for containing said first, second and third unit dosage forms.

It will also be appreciated that, for convenience, any two components of the triple combination may be brought together in a first unit dosage form with the third component in a second unit dosage form.

According to a further aspect of the invention there is provided a triple combination as defined hereinbefore for use in the synergistic treatment of breast cancer.

According to this aspect of the invention there is also provided a pharmaceutical composition for use in the synergistic treatment of breast cancer which comprises a triple combination as defined hereinbefore in association with a pharmaceutically-acceptable excipient or carrier.

As stated above, resistance to endocrine therapy of breast cancer presents a major obstacle. Tumours that respond initially to antihormone treatment later develop resistance that results in tumour progression. Likewise, resistance to the therapy of breast cancer with an EGFR TKI may also develop. In vitro cell models have been developed that reflect the acquisition of resistance of breast cancer cells to both antihormone treatment, for example tamoxifen resistance, and to treatment with an EGFR TKI. It has now been shown that resistance of tamoxifen-resistant MCF7 human breast cancer cells to the EGFR TKI ZD1839 is mediated in part by the elevated expression and activation of components of the Src kinase signalling pathway which allows development of cancer cells having an invasive phenotype. Such cells show an enhancement of cell motility and invasiveness which is reflective of disease progression in vivo.

A particular surprising benefit of this aspect of the present invention is that the breast cancer that can be treated with the triple combination of the invention can be not only breast cancer in patients who have not yet been treated with either antioestrogen therapy or EGFR TKI therapy but also breast cancer that has been treated with either or both of antioestrogen therapy and EGFR TKI therapy and which has not responded to such therapy or which, after initially being treatable with such therapy, has become resistant.

According to a further aspect of the present invention there is provided the use of a triple combination as defined hereinbefore in the manufacture of a medicament for administration to a warm-blooded animal to provide the synergistic treatment of breast cancer.

According to a further aspect of the invention there is provided the use of a triple combination as defined hereinbefore in the manufacture of a medicament for administration to a warm-blooded animal to provide the treatment of antioestrogen-resistant breast cancer.

According to a further aspect of the invention there is provided the use of a triple combination as defined hereinbefore in the manufacture of a medicament for administration to a warm-blooded animal to provide the treatment of EGFR TKI resistant breast cancer.

According to a further aspect of the invention there is provided the use of a triple combination as defined hereinbefore in the manufacture of a medicament for administration to a warm-blooded animal to provide a treatment of breast cancer that is resistant to both antioestrogen and EGFR TKI therapy.

According to a further aspect of the present invention there is provided a method for the synergistic treatment of breast cancer which comprises the administration to a warm-blooded animal that is in need of such treatment of effective amounts of the components of the triple combination as defined hereinbefore.

According to a further aspect of the present invention there is provided a method for the treatment of antioestrogen-resistant breast cancer which comprises the administration to a warm-blooded animal that is in need of such treatment of effective amounts of the components of the triple combination as defined hereinbefore.

According to a further aspect of the present invention there is provided a method for the treatment of EGFR TKI resistant breast cancer which comprises the administration to a warm-blooded animal that is in need of such treatment of effective amounts of the components of the triple combination as defined hereinbefore.

According to a further aspect of the present invention there is provided a method for the treatment of breast cancer that is resistant to both antioestrogen and EGFR TKI therapy which comprises the administration to a warm-blooded animal that is in need of such treatment of effective amounts of the components of the triple combination as defined hereinbefore.

According to this aspect of the present invention there is also provided a method for the synergistic treatment of breast cancer which comprises the administration to a warm-blooded animal that is in need of such treatment of an effective amount of an antioestrogen before, simultaneously with or after the administration of an effective amount of an EGFR TKI, or a pharmaceutically-acceptable salt thereof, as defined hereinbefore, and before, simultaneously with or after the administration of an effective amount of the Src kinase inhibitor AZD0530, or a pharmaceutically-acceptable salt thereof.

According to this aspect of the present invention there is also provided a method for the synergistic treatment of breast cancer which comprises the simultaneous, sequential or separate administration to a warm-blooded animal that is in need of such treatment of effective amounts of the components of the triple combination as defined hereinbefore.

According to this aspect of the present invention there is also provided a method for the synergistic treatment of breast cancer which comprises the administration to a warm-blooded animal that is in need of such treatment of an effective amount of an antioestrogen as defined hereinbefore and the simultaneous, sequential or separate administration of an effective amount of an EGFR TKI, or a pharmaceutically-acceptable salt thereof, as defined hereinbefore and the simultaneous, sequential or separate administration of an effective amount of the Src kinase inhibitor AZD0530, or a pharmaceutically-acceptable salt thereof.

The present invention also relates to a triple combination comprising an antioestrogen, an EGFR TKI, or a pharmaceutically-acceptable salt thereof, and the Src kinase inhibitor AZD0530, or a pharmaceutically-acceptable salt thereof, for use in the delay of the progression of breast cancer from a hormonally responsive to a hormonally non-responsive state i.e. to inhibit the transformation of breast cancer cells from a hormone-dependent, non-invasive state into a hormone-independent, more invasive state. Consequently the triple combination has a beneficial effect on the time to disease progression and the survival rate.

According to this aspect of the present invention there is provided a triple combination comprising an antioestrogen, an EGFR TKI, or a pharmaceutically-acceptable salt thereof, and the Src kinase inhibitor AZD0530, or a pharmaceutically-acceptable salt thereof, for use in the delay of the progression of breast cancer from a hormonally responsive to a hormonally non-responsive state.

In another aspect, the invention relates to the use of the triple combination to inhibit the transformation of breast cells into cancerous cells i.e. the combination of compounds provides a breast cancer chemopreventative effect.

We have found that unexpectedly the triple combination of the present invention has effects not only on the growth of transformed breast cancer cells but also on the constitutive growth of normal cells and of non-malignant, abnormal cells in the breast. The triple combination of the present invention may therefore be used to reduce, preferably to inhibit, the transformation of breast cells to a malignant state. The triple combination of an antioestrogen, an EGFR TKI and the Src kinase inhibitor AZD0530 of the present invention can inhibit the transformation of normal breast cells to a DCIS state. Said triple combination can also inhibit the transformation of DCIS cells to a malignant state.

It is further expected that the triple combination will have a beneficial effect in preventing the onset of breast cancer in women genetically predisposed to the disease.

According to this aspect of the present invention there is provided a triple combination comprising an antioestrogen, an EGFR TKI, or a pharmaceutically-acceptable salt thereof, and the Src kinase inhibitor AZD0530, or a pharmaceutically-acceptable salt thereof, for use in reducing, preferably inhibiting, the transformation of normal breast cells to a DCIS state.

According to this aspect of the present invention there is also provided a triple combination comprising an antioestrogen, an EGFR TKI, or a pharmaceutically-acceptable salt thereof, and the Src kinase inhibitor AZD0530, or a pharmaceutically-acceptable salt thereof, for use in reducing, preferably inhibiting, the transformation of normal breast cells or DCIS cells to a malignant state.

A triple combination treatment of the present invention as defined hereinbefore may be administered as a sole therapy or may in addition involve surgery or radiotherapy or the administration of a chemotherapeutic agent as defined hereinbefore.

Biological Test Procedures

The following test methods may be used to demonstrate the activity of the Src kinase inhibitor AZD0530 when used in combination with an antioestrogen and/or an EGFR TKI.

(a) Cell Growth Studies

Various test methods have been described by Knowlden et al., *Endocrinology*, 2003, 144, 1032-1044 and include one or more of:—

(i) tamoxifen-responsive 'wild type' MCF7 human breast cancer cells;
(ii) an endocrine-insensitive variant of such MCF7 breast cancer cells that was designated 'Tam-R' (tamoxifen-resistant); and
(iii) a variant of such 'TAM-R' cells that was also insensitive to treatment with the EGFR TKI ZD1839 that was designated 'Tam/TKI-R'.

Tamoxifen-responsive 'wild type' MCF7 breast cancer cells were routinely cultured in phenol red-free RPMI medium supplemented with 5% foetal calf serum plus penicillin (10 IU/ml), streptomycin (10 µg/ml) and fungizone (2.5 µg/ml). Cultures were maintained at 37° C. in a humidified atmosphere with 5% $CO_2$. When used for experimental analysis in the assays described below the cells were maintained in phenol red-free RPMI medium supplemented with 5% charcoal-stripped, steroid-depleted foetal calf serum, antibiotics as above and glutamine (200 mM).

'Tam-R' MCF7 breast cancer cells were maintained in phenol red-free RPMI medium supplemented with 5% charcoal-stripped, steroid-depleted foetal calf serum, antibiotics as above, glutamine (200 mM) and 4-hydroxytamoxifen ($10^{-7}$M in ethanol).

'Tam/TKI-R' MCF7 breast cancer cells were obtained by the continuous exposure of 'Tam-R' MCF7 breast cancer cells to ZD1839 ($10^{-6}$M) for a period of 12 months.

Nunc (Rosklide, Denmark) tissue culture plasticware was used.

Cell monolayers were grown for 7 days in serum growth factor free DCCM medium in the presence of increasing concentrations of the individual components of the above-mentioned combinations or with the combinations themselves. Cell population growth was evaluated by means of trypsin dispersion of the cell monolayers and cell number was measured using a Beckman Coulter counter (available from Beckman Coulter Limited, Luton, GB). All cell growth experiments were performed in triplicate.

(b) Time Lapse Analysis of Cell Motility

Cells were cultured in 6-well tissue-culture plates and allowed to reach log phase growth. Plates were transferred to the heated stage of an inverted microscope and cell cultures were overlaid with mineral oil to minimise pH changes in the medium during the cell motility analysis. Cell motility was recorded over a period of 6 hours using a video camera coupled to a time lapse video recording system. For quantitation of cell motility, images were captured at 10 minute intervals during video playback and the movement of at least 10 individual cells was tracked using Optimas image analysis software (Media Cybernetics UK, Finchampstead, Berkshire, GB). Cell movement was plotted as either cell position (x-position vs. y-position) or total distance migrated (μm) as a function of time. To determine the directional persistence of cell motility, paths of cells were plotted such that all paths start from the origin.

(c) Wound Healing Assay

Exponentially growing cells were harvested and plated onto 24-well cell culture plates. After establishment of monolayer cultures, cells were wounded by manual scratching with a pipette tip and washed with phosphate-buffered serum (PBS). Fresh medium containing appropriate growth factors, inhibitor compounds (or combinations of inhibitor compounds) was added. After 36 hours, the cells were fixed with 4% formaldehyde, stained with crystal violet (0.5% in PBS) and wounds were photographed at 20-fold magnification. Some wells were fixed and stained directly after wounding (t=0 hour time point) to allow calculation of per-cent wound healing.

(d) Fibronectin Cell Migration Assay

The polycarbonate filter membranes of Transwell chambers (6.5 mm diameter, 8.0 μm pore size from Costar Inc., Cambridge, Mass., USA) were coated on the underside of the membrane with 50 μg/ml fibronectin in serum-free RPMI for 2 hours at 37° C. The polycarbonate membranes were rinsed once with PBS. Cells were harvested and resuspended at a concentration of $5 \times 10^5$ cells per ml in serum-free RPMI. Aliquots of cells (100 μl; $5 \times 10^4$ cells) were seeded into each well to which 500 μl of experimental medium had been added. In control experiments, cells were allowed to migrate toward the underside of the membrane for 20 hours. In test experiments, appropriate concentrations of inhibitor compounds (or combinations of inhibitor compounds) were added and cells were allowed to migrate toward the underside of the membrane for 20 hours. The non-migratory cells on the upper side of the membrane were removed with a cotton swab and the migratory cells attached to the underside of the membrane were fixed in 4% formaldehyde and stained with 0.5% crystal violet for 10 minutes at ambient temperature. The number of migrating cells was counted at 20-fold magnification using an inverted microscope.

(e) Cell Invasion Assay

A modification of the method previously described by Hiscox et al. (*Breast Cancer Research Treatment*, 2000, 59, 245-254) was used to study the invasive nature of the breast cancer cells.

Transwell polycarbonate filter membrane inserts (6.5 mm diameter, 8 μm pore size from Costar Inc.) were placed in 24-well tissue-culture plates and were coated with Matrigel (0.4 μg/ml) at ambient temperature overnight in a sterile tissue culture hood. After rehydrating the wells with serum-free RPMI for 1 hour at 37° C., cells were seeded onto the membrane inserts at $5 \times 10^4$ cells/well with or without appropriate concentrations of inhibitor compounds (or combinations of inhibitor compounds) and 600 μl of culture medium was added such that the membrane inserts were immersed. The wells were cultured at 37° C. for 72 hours, after which the non-invasive cells and Matrigel were removed from the inside of the wells with a cotton swab. Those cells that had invaded through to the underside of the membrane were fixed with 4% formaldehyde and the porous membranes were removed from the invasion chamber using a scalpel blade and mounted onto glass microscope slides (using Vectashield from Molecular Probes, Eugene, Oreg., USA) containing the nuclear stain, DAPI. Cell invasion was quantified with a fluorescent microscope by viewing 5 separate fields per membrane at 2-fold magnification and counting the number of cells in each field. Data were plotted as either mean cells per field±SEM or per-cent invasion with respect to the control.

(f) Cell Attachment Assay

The wells of a 96-well plate were coated with Matrigel (50 μg/well) and air-dried overnight in a sterile tissue culture hood. Cells growing in log phase were harvested and adjusted to a concentration of $2 \times 10^5$ cells per ml in culture medium containing appropriate concentrations of inhibitor compounds (or combinations of inhibitor compounds). Aliquots of cells ($2 \times 10^4$ cells) were seeded into each well and the plate was incubated at 37° C. for 30 minutes. The wells were washed twice with PBS to remove unbound cells prior to the addition to each well of 150 μl of MTT solution (0.5 mg/ml in serum-free medium). Plates were incubated for a further 4 hours at 37° C. to allow the development of tetrazolium crystals within the cells. The MTT solution was removed from the wells and the dye was extracted at 4° C. overnight with 10% TX-100 solution. The absorbance was measured with a Titerteck Multiskan ELISA plate reader (Flow Laboratories, UK) equipped with a 540 nm filter. Cell attachment in response to the treatments was calculated as a percentage of the cells adhered in the control (untreated) wells.

(g) In Vitro c-Src Transfected NIH 3T3 (c-Src 3T3) Fibroblast Proliferation Assay This assay determined the ability of a test compound (or combination of test compounds) to inhibit the proliferation of National Institute of Health (NIH) mouse 3T3 fibroblast cells that had been stably-transfected with an activating mutant (Y530F) of human c-Src.

Using a similar procedure to that described by Shalloway et al., *Cell*, 1987, 49, 65-73, NIH 3T3 cells were transfected with an activating mutant (Y530F) of human c-Src. The resultant c-Src 3T3 cells were typically seeded at $1.5 \times 10^4$ cells per well into 96-well tissue-culture-treated clear assay plates (Costar) each containing an assay medium comprising Dulbecco's modified Eagle's medium (DMEM; Sigma) plus 0.5% foetal calf serum (FCS), 2 mM glutamine, 100 units/ml penicillin and 0.1 mg/ml streptomycin in 0.9% aqueous sodium chloride solution. The plates were incubated overnight at 37° C. in a humidified (7.5% $CO_2$: 95% air) incubator.

Test compounds were solubilised in DMSO to form a 10 mM stock solution. Aliquots of the stock solution were diluted with the DMEM medium described above and added to appropriate wells. Serial dilutions were made to give a range of test concentrations. Control wells to which test compound was not added were included on each plate. The plates were incubated overnight at 37° C. in a humidified (7.5% $CO_2$: 95% air) incubator.

BrdU labelling reagent (Boehringer Mannheim Catalogue No. 647 229) was diluted by a factor of 1:100 in DMEM medium containing 0.5% FCS and aliquots (20 μl) were added to each well to give a final concentration of 10 μM). The plates were incubated at 37° C. for 2 hours. The medium was decanted. A denaturing solution (FixDenat solution, Boehringer Mannheim Catalogue No. 647 229; 50 μl) was added to each well and the plates were placed on a plate shaker at ambient temperature for 45 minutes. The supernatant was decanted and the wells were washed with PBS (200 μl per well). Anti-BrdU-Peroxidase solution (Boehringer Mannheim Catalogue No. 647 229) was diluted by a factor of 1:100 in PBS containing 1% BSA and 0.025% dried skimmed milk (Marvel (registered trade mark), Premier Beverages, Stafford, GB) and an aliquot (100 μl) of the resultant solution was added to each well. The plates were placed on a plate shaker at ambient temperature for 90 minutes. The wells were washed with PBS (×5) to ensure removal of non-bound antibody conjugate. The plates were blotted dry and tetramethylbenzidine substrate solution (Boehringer Mannheim Catalogue No. 647 229; 100 μl) was added to each well. The plates were gently agitated on a plate shaker while the colour developed during a 10 to 20 minute period. The absorbance of the wells was measured at 690 nm. The extent of inhibition of cellular proliferation at a range of concentrations of each test compound (or combination of test compounds) was determined and an anti-proliferative $IC_{50}$ value was derived.

(h) In Vitro Microdroplet Migration Assay

This assay determines the ability of a test compound (or combination of test compounds) to inhibit the migration of adherent mammalian cell lines, for example the human tumour cell line A549.

RPMI medium (Sigma) containing 10% FCS, 1% L-glutamine and 0.3% agarose (Difco Catalogue No. 0142-01) was warmed to 37° C. in a water bath. A stock 2% aqueous agar solution was autoclaved and stored at 42° C. An aliquot (1.5 ml) of the agar solution was added to RPMI medium (10 ml) immediately prior to its use. A549 cells (Accession No. ATCC CCL185) were suspended at a concentration of $2 \times 10^7$ cells/ml in the medium and maintained at a temperature of 37° C.

A droplet (2 μl) of the cell/agarose mixture was transferred by pipette into the centre of each well of a number of 96-well, flat bottomed non-tissue-culture-treated microtitre plate (Bibby Sterilin Catalogue No. 642000). The plates were placed briefly on ice to speed the gelling of the agarose-containing droplets. Aliquots (90 μl) of medium which had been cooled to 4° C. were transferred into each well, taking care not to disturb the microdroplets. Test compounds were diluted from a 10 mM stock solution in DMSO using RPMI medium as described above. Aliquots (10 μl) of the diluted test compounds were transferred to the wells, again taking care not to disturb the microdroplets. The plates were incubated at 37° C. in a humidified (7.5% $CO_2$ : 95% air) incubator for about 48 hours.

Migration was assessed visually and the distance of migration was measured back to the edge of the agar droplet. A migratory inhibitory $IC_{50}$ was derived by plotting the mean migration measurement against test compound(s) concentration.

(i) In Vivo Xenograft Growth Assays

This test measures the ability of combination product of the invention to inhibit the growth of human and/or mouse carcinomas grown as tumours in athymic nude mice. Suitable cancer cells for injection include human MCF7 breast cancer cells (obtainable from American Type Culture Collection, 10801 University Boulevard, Manassas, Va. 20110-2209; Cat. No. HTB-22), c-Src transfected mouse 3T3 fibroblast cancer cells (transfection with an activating mutant (Y530F) of human c-Src via a similar procedure to that described by Shalloway et al., *Cell,* 1987, 49, 65-73), human LoVo colorectal cancer cells (obtainable from European Collection of Cell Cultures, ECACC, CAMR, Salisbury, Wiltshire, SP4 0JG, UK; Cat. No. CCL 229), human CaLu-6 lung cancer cells (ATCC Cat. No. HTB-56) and human A549 NSCLC cancer cells (ATCC Cat. No. CCL185).

A total of about $1 \times 10^6$ human cancer cells in 0.1 ml of a 1:1 mixture of matrigel (Beckton Dickinson Catalogue No. 40234) and Eagle's Minimum Essential Medium (EMEM; Gibco Catalogue No 21090-022) were injected subcutaneously into a flank of each test mouse and the resultant tumours were allowed to grow for about 10 days. Animals were selected to provide control and treatment groups of approximately equal average tumour volume. Each combination product was prepared as a ball-milled suspension in 1% polysorbate-80 vehicle (0.1 ml per 10 g body weight at the appropriate test dose) and dosed orally once daily commencing on day 10 for a period of about 28 days. Tumour size was measured twice weekly using callipers and a theoretical volume was calculated. The effect on tumour growth was assessed.

In general, activity possessed by the Src kinase inhibitor AZD0530 when used alone may be demonstrated at the following concentrations or doses in one or more of the above tests:—

Test (a):—$IC_{50}$ in the range, for example, 0.1-5 μM;
Test (b):—$IC_{50}$ in the range, for example, 0.1-1 μM;
Test (d):—$IC_{50}$ versus 'Tam-R' cells of approximately 0.1 μM;
Test (e):—$IC_{50}$ versus 'Tam-R' cells of approximately 0.1 μM;
Test (f):—$IC_{50}$ in the range, for example, 0.1-1 μM;
Test (g):—activity in the range, for example, 0.1-5 μM;
Test (h):—activity in the range, for example, 0.1-5 μM;
Test (i):—activity in the range, for example, 1-200 mg/kg/day.

In general, when the Src kinase inhibitor AZD0530 is used in combination with an antioestrogen and/or an EGFR TKI in one or more of the above tests, increased activity may be demonstrated over that seen with AZD0530 alone. Alternatively, activity possessed by the Src kinase inhibitor AZD0530 when used in combination with an antioestrogen and/or an EGFR TKI may be demonstrated at lower concentrations or doses in one or more of the above tests.

For example, when a combination of AZD0530 (0.1 μM) and ZD1839 (1 μM) is used against 'Tam-R' cells, the following activity may be demonstrated:—

Test (d):—an approximately $IC_{70}$ effect;
Test (e):—an approximately $IC_{70}$ effect;

and when a combination of AZD0530 (1 μM) and ZD1839 (1 μM) is used against 'Tam-R' cells, the following activity may be demonstrated:—

Test (d):—an approximately $IC_{85}$ effect;
Test (e):—an approximately $IC_{75}$ effect.

The invention claimed is:

1. A method for treating breast cancer which comprises administering to a warm-blooded animal that is in need of such treatment effective therapeutic amounts of the components of a pharmaceutical combination of anti-cancer compounds, the pharmaceutical combination comprising as active components:
   (a) an antioestrogen selected from the group consisting of tamoxifen,
      non-steroidal aromatase inhibitors anastrazole and letrozole and steroidal aromatase inhibitor exemstane,
   wherein the tamoxifen is administered at a daily dose of between 5 and 30 mg; the anastrazole and letrozole are administered at a daily dose of between 0.005 and 25 mg; and the exemstane is administered at a daily dose of between 10 and 40 mg; and
   (b) the Src kinase inhibitor AZD0530, or a pharmaceutically-acceptable salt thereof, wherein the AZD0530 is administered at a daily dose of between 25 mg and 250 mg.

2. A method for treating antioestrogen-resistant breast cancer which comprises administering to a warm-blooded animal that is in need of such treatment effective therapeutic amounts of the components of a pharmaceutical combination of anti-cancer compounds, the pharmaceutical combination comprising as active components:
   (a) an antioestrogen selected from the group consisting of tamoxifen, non-steroidal aromatase inhibitors anastrazole and letrozole and steroidal aromatase inhibitor exemstane, wherein the tamoxifen is administered at a daily dose of between 5 and 30 mg; the anastrazole and letrozole are administered at a daily dose of between 0.005 and 25 mg; and the exemstane is administered at a daily dose of between 10 and 40 mg; and (b) the Src kinase inhibitor AZD0530, or a pharmaceutically-acceptable salt thereof, wherein the AZD0530 is administered at a daily dose of between 25 mg and 250 mg.

3. A method for delaying the progression of breast cancer from a hormonally responsive to a hormonally non-responsive state which comprises administering to a warm-blooded animal that is in need of such treatment effective therapeutic amounts of the components of a pharmaceutical combination of anti-cancer compounds, the pharmaceutical combination comprising as active components:

(a) an antioestrogen selected from the group consisting of tamoxifen,
non-steroidal aromatase inhibitors anastrazole and letrozole and steroidal aromatase inhibitor exemstane, wherein the tamoxifen is administered at a daily dose of between 5 and 30 mg; the anastrazole and letrozole are administered at a daily dose of between 0.005 and 25 mg; and the exemstane is administered at a daily dose of between 10 and 40 mg; and (b) the Src kinase inhibitor AZD0530, or a pharmaceutically-acceptable salt thereof, wherein the AZD0530 is administered at a daily dose of between 25 mg and 250 mg.

4. A method for reducing the transformation of normal breast cells to a DCIS state which comprises administering to a warm-blooded animal that is in need of such treatment effective therapeutic amounts of the components of a pharmaceutical combination of anti-cancer compounds, the pharmaceutical combination comprising as active components:

(a) an antioestrogen selected from the group consisting of tamoxifen,
non-steroidal aromatase inhibitors anastrazole and letrozole and steroidal aromatase inhibitor exemstane, wherein the tamoxifen is administered at a daily dose of between 5 and 30 mg; the anastrazole and letrozole are administered at a daily dose of between 0.005 and 25 mg; and the exemstane is administered at a daily dose of between 10 and 40 mg; and (b) the Src kinase inhibitor AZD0530, or a pharmaceutically-acceptable salt thereof wherein the AZD0530 is administered at a daily dose of between 25 mg and 250 mg.

5. A method for reducing the transformation of normal breast cells or DCIS cells to a malignant state which comprises administering to a warm-blooded animal that is in need of such treatment effective therapeutic amounts of the components of a pharmaceutical combination of anti-cancer compounds, the pharmaceutical combination comprising as active components:

(a) an antioestrogen selected from the group consisting of tamoxifen,
non-steroidal aromatase inhibitors anastrazole and letrozole and steroidal aromatase inhibitor exemstane, wherein the tamoxifen is administered at a daily dose of between 5 and 30 mg; the anastrazole and letrozole are administered at a daily dose of between 0.005 and 25 mg; and the exemstane is administered at a daily dose of between 10 and 40 mg; and (b) the Src kinase inhibitor AZD0530, or a pharmaceutically-acceptable salt thereof wherein the AZD0530 is administered at a daily dose of between 25 mg and 250 mg.

* * * * *